United States Patent
Deutsch

(10) Patent No.: US 7,008,223 B2
(45) Date of Patent: Mar. 7, 2006

(54) ENDODONTIC INSTRUMENT FOR ACCESSING A PULP CHAMBER

(75) Inventor: Allan S. Deutsch, New York, NY (US)

(73) Assignee: Essential Dental Systems, Inc., South Hackenaack, NJ (US)

( * ) Notice: Subject to any disclaimer, the term of this patent is extended or adjusted under 35 U.S.C. 154(b) by 90 days.

(21) Appl. No.: 10/717,066

(22) Filed: Nov. 19, 2003

(65) Prior Publication Data

US 2005/0106532 A1    May 19, 2005

(51) Int. Cl.
*A61C 5/02*    (2006.01)
(52) U.S. Cl. .................................... 433/102
(58) Field of Classification Search ............. 433/102, 433/165, 72, 75
See application file for complete search history.

(56) References Cited

U.S. PATENT DOCUMENTS

| 3,562,913 A | * | 2/1971 | Saffro ................... 433/75 |
| 3,961,422 A | | 6/1976 | Riitano |
| 3,962,791 A | | 6/1976 | Zdarsky |
| 4,345,899 A | * | 8/1982 | Vlock ................... 433/165 |
| 5,429,504 A | * | 7/1995 | Peltier et al. ........... 433/165 |
| 6,042,376 A | * | 3/2000 | Cohen et al. ........... 433/102 |
| 6,390,814 B1 | | 5/2002 | Gardiner |
| 6,739,872 B1 | * | 5/2004 | Turri .................... 433/75 |
| 2002/0172923 A1 | * | 11/2002 | Strong et al. ........... 433/165 |

\* cited by examiner

*Primary Examiner*—Cary E. O'Connor
(74) *Attorney, Agent, or Firm*—Lerner, David, Littenberg, Krumholz & Mentlik, LLP

(57) ABSTRACT

An endodontic instrument for accessing a pulp chamber of a molar includes an elongated shaft having an upper end and a lower end and a stop fixed to the shaft at a distance between 6–8 mm from the lower end. The instrument also includes a cutting head located along the shaft adjacent the lower end. In certain embodiments, the cutting head has an annular cutting surface extending about a first circumferential portion of the cutting head and a flat non-cutting surface extending about a second circumferential portion of the cutting head. The lower end of the shaft may have a pointed tip.

22 Claims, 7 Drawing Sheets

ENDODONTIC INSTRUMENT FOR ACCESSING A PULP CHAMBER

BACKGROUND OF THE INVENTION

The present invention is generally related to endodontic instruments and is more particularly related to an endodontic instrument used to drill an access opening into a pulp chamber of a molar.

A molar includes a crown that projects above a gum line and a root that is secured within a jaw bone. The inside of the molar has a pulp chamber and root canal system through which blood vessels, nerves and connective tissue (hereinafter referred to as "pulp tissue") extends. The pulp tissue extends from the crown of the tooth to the lower end of the roots where it connects to bone surrounding the root of the tooth.

Frequently, the pulp chamber or root canal of a tooth becomes infected or inflamed. These problems may be caused by repeated dental procedures on the tooth, a crack in the tooth, blunt trauma to the tooth or tooth decay. The symptoms generally associated with an infected or inflamed pulp chamber include sensitivity to heat or cold, swelling and tenderness in the nearby gums, pain and/or discoloration of the tooth. Failure to treat an infected or inflamed pulp chamber may eventually lead to the formation of an abscess and/or cause severe pain.

An endodontic procedure is typically used to treat a tooth having an infected or inflamed pulp chamber. In endodontic therapy, commonly referred to as root canal, a dentist operates on a diseased pulp by removing the diseased pulp tissue and filling in the pulp chamber and the root canal with biocompatible material. Initially, the dentist must gain access to the pulp chamber using a cutting instrument for drilling into the crown of the tooth until the dental instrument reaches the pulp chamber. Dentists typically rely on tactile senses when accessing the pulp chamber. As the dentist drills through dentin, the dentist senses a level of resistance to advancement of the drill, however the level of resistance decreases once the drill reaches the less dense pulp chamber. Once the pulp chamber has been reached, the dentist will remove the diseased pulp tissue from the pulp chamber so as to expose upper ends of the root canals. The dentist may then use a thin, elongated file adapted to fit into the relatively narrow root canals so as to remove all of the pulp tissue from the canals. Once the tissue has been removed from the canals, the dentist irrigates the canals to remove pulpal remnants. Finally, the dentist uses other elongated instruments to widen the root canals and remove irregularities in the canals so that a filling material can be introduced into the canals. Most root canal filling materials comprise biocompatible, thermoplastic material such as gutta purcha.

There have been a number of efforts directed to limiting the depth of penetration of an endodontic instrument into a root canal. For example, U.S. Pat. No. 3,961,422 to Riitano discloses an endodontic file for opening a root canal including a stop for limiting the depth of penetration of the file into the root canal. The '422 patent discloses a bifurcated disk having a central instrument-receiving bore that is made of two disc halves. After the elongated file has been passed through the central bore of the disc, a resilient snap-ring is seated on a circumferential groove surrounding the bifurcated disc to secure the two disc halves of the stop together.

U.S. Pat. No. 6,390,814 to Gardiner discloses another endodontic file having a stop that limits insertion of the file into a root canal.

U.S. Pat. No. 3,962,791 to Zdarsky discloses yet another endodontic file having a stop that limits how far the file can be inserted into the root canal of a tooth. The stop includes a two-part housing having a through-going passage and a compression spring positioned in the passage having an inner diameter that is normally smaller than the outer diameter of the shaft of the file. During assembly, the stop is slipped over the shaft of the root canal file, whereby the compression spring grasps the shaft for preventing sliding of the stop along the shaft. The stop may be slid along the shaft by first rotating the two parts of the housing relative to each other for loosening the spring from the shaft.

When performing a root canal on a molar tooth, a dentist must gain access to the pulp chamber of the molar. Unfortunately, perforations of the furcation of the tooth may occur when accessing the pulp chamber. Typically, a dentist relies on tactile sense when drilling into the pulp chamber of a molar. Generally, the level of resistance is greater when the dentist is drilling through the dentin of the molar, however, the level of resistance is reduced when the drill reaches the pulp chamber. This phenomenon occurs because the density of matter in the pulp chamber is less than the density of the dentin region of the molar. Even though dentists are extremely focused on sensing when the drill transitions from the dentin to the pulp chamber, accidental perforation of the pulp chamber floor and the furcation occur on a regular basis. As is well know to those skilled in the art, a perforation of the furcation of a multi-rooted tooth is a serious complication.

Although the prior art provides numerous endodontic files having stops for limiting penetration of the file into a root canal, the prior art provides no endodontic instruments used to access a pulp chamber of a tooth, whereby the instrument has a stop for preventing perforation of the floor of a pulp chamber or the furcation of a tooth. Thus, there is a need for an endodontic instrument used to drill an access opening into a pulp chamber of a tooth, whereby the instrument has a stop to prevent or limit insertion of the instrument into the tooth. These and other preferred embodiments of the present invention will be described in more detail below.

SUMMARY OF THE INVENTION

The present application is directed to an endodontic instrument used for drilling into the pulp chamber of a mandibular or maxillary molar. The endodontic instrument has preferably been designed to insure that the pulp chamber is reliably accessed without perforating the pulp chamber floor or the furcation of the molars. In other preferred embodiments, the endodontic instrument may be used to drill into the pulp chamber of any tooth having a furcation, such as a molar or a bicuspid.

In certain preferred embodiments of the present invention, an endodontic instrument includes an elongated shaft having an upper end and a lower end, and a stop fixed to the shaft at a distance between 6–8 mm from the lower end. The stop is preferably permanently fixed to the shaft of the instrument. The stop fixed to the shaft may be circular or have another geometric shape, such as a polygon. The endodontic instrument also preferably includes a cutting head located along the shaft adjacent the lower end thereof. In certain preferred embodiments, the cutting head preferably has an annular cutting surface extending about a first circumferential portion of the cutting head and a flat non-cutting surface extending about a second circumferential portion of the cutting head. The annular cutting surface preferably includes a spherical cutting surface having cutting edges provided thereon. In other preferred embodiments, the lower end of the shaft has a tip, such as a pointed tip. The tip desirably projects beyond a lower end of the cutting head.

As noted above, the stop prevents the endodontic instrument from being inserted too far into the molar, which could cause perforation of the pulp chamber floor or the furcation. Based upon an in vitro study measuring the critical morphology of molar pulp chambers, it has been determined that the pulp chamber ceiling in virtually all instances falls between a range of approximately 6–8 mm from the cusp tips of the molars. Thus, placing the stop at a distance of approximately 6–8 mm from the lower end of the endodontic instrument will reliably insure that the pulp chamber has been reached by the instrument without perforating the floor of the pulp chamber or the furcation of the molar. In other preferred embodiments, the stop is fixed to the shaft at a distance between 6.5–7.5 mm from the lower end of the shaft. In more preferred embodiments, the stop is fixed to the shaft at a distance of approximately 6.75–7.25 mm from the lower end of the shaft. In even more preferred embodiments of the present invention, the stop is fixed to the shaft at a distance of approximately 7 mm from the lower end of the shaft.

In certain preferred embodiments, the stop is rigid and is permanently fixed to the shaft. The shaft may also have an exterior surface including an annular groove whereby the stop is assembled with the shaft so that the stop is secured at least partially within the annular groove.

In certain preferred embodiments, the flat non-cutting surface of the cutting head preferably tapers inwardly between the upper and lower ends of the shaft. The flat non-cutting surface desirably tapers inwardly from the upper end of the shaft toward the lower end of the shaft at approximately 4–6 degrees. In more preferred embodiments, the flat non-cutting surface tapers inwardly at approximately 5 degrees. In still other preferred embodiments, the flat non-cutting surface may not taper at all. The cutting head has the annular cutting surface which extends about the first circumferential portion of the cutting head. The annular cutting surface desirably has cutting edges formed therein. In certain preferred embodiments, cutting edges are projections. In other preferred embodiments, the cutting edges have a helical pattern. The cutting head desirably has a cross-sectional diameter that is greater than a cross-sectional diameter of the section of the shaft located directly above the cutting head. As such, the outer perimeter of the cutting head preferably extends beyond the outer exterior surface of the section of the shaft located directly above the cutting head.

In other preferred embodiments of the present invention, an endodontic instrument for accessing the pulp chamber of mandibular and maxillary molars includes an elongated shaft having an upper end and a lower end, a pointed tip provided at the lower end of the shaft and a rigid stop immovably fixed to the shaft at a distance between 6–8 mm from the pointed tip. The endodontic instrument also preferably includes a cutting head located along the shaft adjacent the pointed tip. The cutting head desirably has an annular cutting surface extending about a first circumferential portion of the cutting head and a flat non-cutting surface extending about a second circumferential portion of the cutting head.

During an endodontic procedure, the upper end of the endodontic instrument is preferably secured to a dental drill. In order to access the pulp chamber of a molar, the cutting head of the instrument is abutted against the crown of the molar. As the drill rotates the instrument at a high speed, a downward force is applied through the instrument and onto the crown of the molar so that the cutting head begins to cut through the enamel layer and dentin layer of the molar. As the cutting head cuts through the pulp chamber ceiling of the molar, the stop is adapted to abut against one or more cusp tips of the molar so as to prevent further advance of the cutting head. Based upon the results of the above-mentioned study measuring critical morphology of molar pulp chambers, the stop has been placed at a distance from the pointed tip that will prevent perforation of the pulp chamber floor and the furcation of the molar.

After the pulp chamber has been accessed using the endodontic instrument described above, a shaper bur is passed through the access opening for widening the interior axial walls of the opening. As the interior axial walls of the opening are widened, the upper ends of the root canals at the bottom of the pulp chamber are exposed. Thin, elongated files may then be used to remove pulp tissue from the root canals as part of a root canal procedure.

These and other preferred embodiments of the present invention will be described in more detail below.

DETAILED DESCRIPTION

A study was conducted to measure key anatomical landmarks relating to pulp chamber morphology in mandibular and maxillary molars. One hundred human mandibular molars and one hundred human maxillary molars were randomly selected for the study. The randomly selected mandibular and maxillary molar samples were gathered from oral surgery and denture center practices. None of the teeth were crowned, however, some of the teeth contained caries and/or restorations. Teeth in which the caries and/or restorations violated the pulp chamber were rejected and not used in the study. The age, gender and systemic condition of the patients from which the molars were collected was unknown.

Before measurements were taken, each tooth was mounted using wax on a periodontal millimeter x-ray grid. The teeth were mounted perpendicular to the grid in a mesiodistal direction, which is the same x-ray orientation that is recorded in vivo. The x-rays were taken using a heliodent machine set on the molar setting with a numerical value of 25. Each x-ray was developed in an automatic developer sold by Air Techniques of Farmingdale, N.Y., and was examined using a stereoscopic microscope sold by Bausch & Lomb of Rochester, N.Y. The stereoscopic microscope used a magnification of 10×. All measurements were made by the same individual and recorded to the nearest 0.5 mm.

Figure 1:
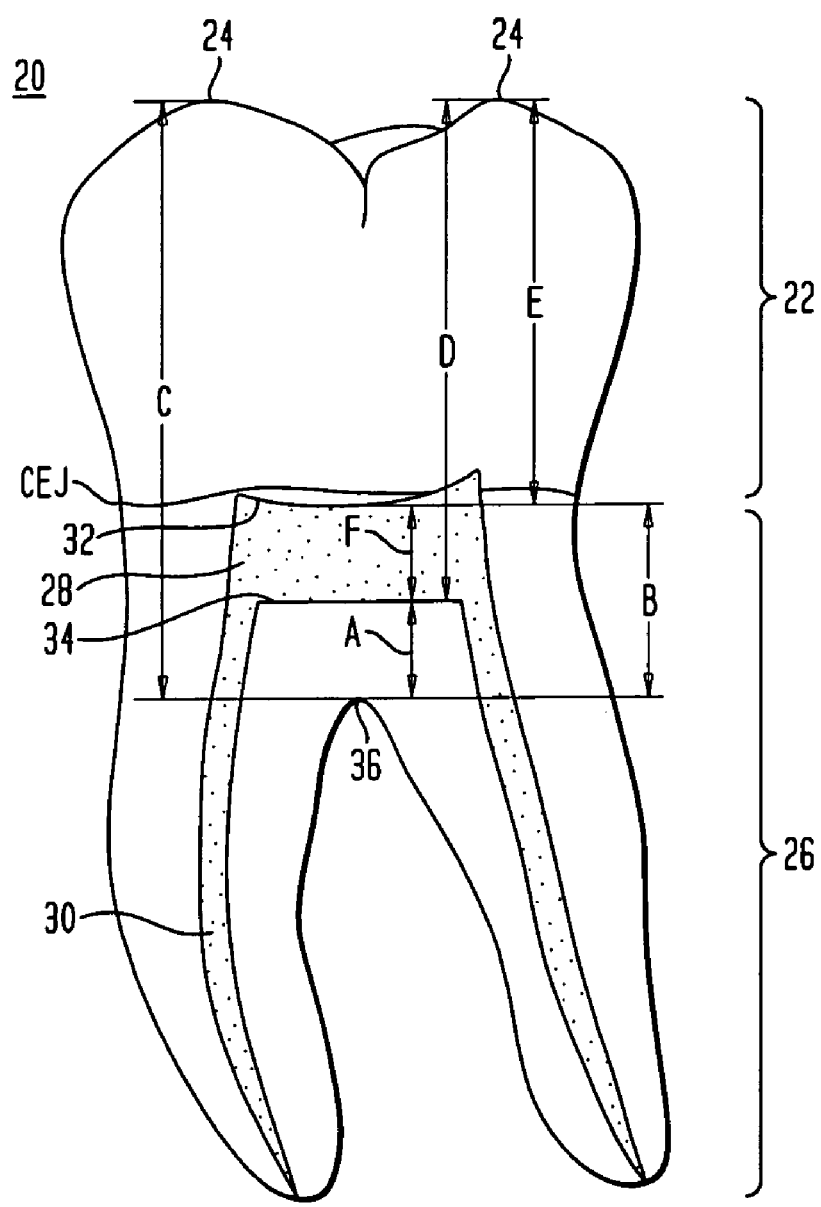
FIG. 1 shows a cross-sectional view of a mandibular molar.

FIG. 1 shows a typical mandibular molar analyzed in the study. The mandibular molar 20 includes a crown 22 having cusps 24 and a root 26. The molar 20 includes a pulp chamber 28 containing pulp tissue (not shown) and two or more root canals 30 extending through the root 26 thereof. The root canals 30 also include pulp tissue (not shown) that extends from a lower end of the root 26. Three direct measurements were taken of each mandibular molar. The measurement designated by the letter "A" represents the distance between the pulp chamber floor 34 and the closest point to the furcation 36. The measurement designated by the letter "B" represents the distance between the pulp chamber ceiling 32 to the closest point to the furcation 36. The measurement designated by the letter "C" represents the distance from the buccal cusp tip 24 of the molar 20 to the closest point to the furcation 36. The measurement designated by the letter "D" represents the distance from the buccal cusp tip 24 to the pulp chamber floor 34. The measurement designated by the letter "E" represents the distance from the buccal cusp tip 24 to the pulp chamber ceiling 32. The measurement designated by the letter "F" represents the distance between the pulp chamber ceiling 32 and the pulp chamber floor 34, i.e. the height of the pulp chamber. The x-ray analysis of the tooth also noted whether the pulp chamber ceiling 32 was located above, below or at the level of the Cemento-Enamel Junction (CEJ).

Figure 2:
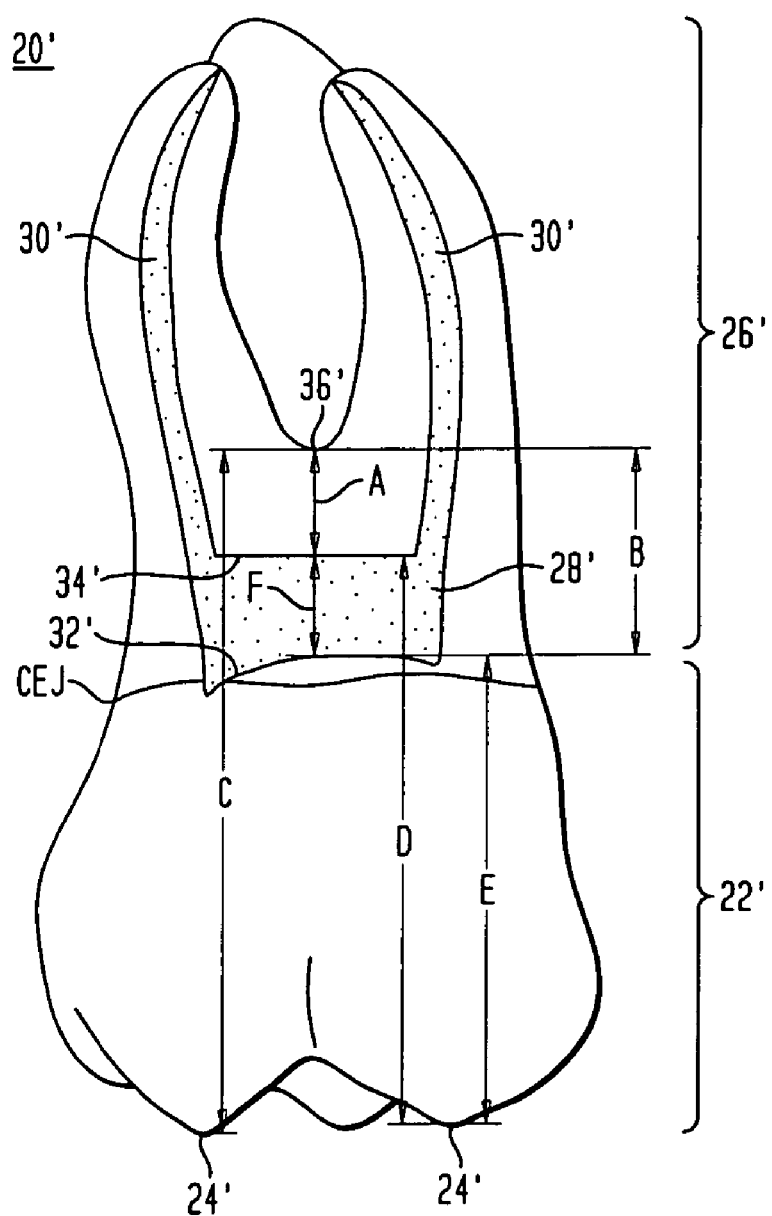
FIG. 2 shows a cross-sectional view of a maxillary molar.

Referring to FIG. 2, direct measurements were also taken on each maxillary molar 20'. The measurement designated by the letter "A" represents the distance between the pulp chamber floor 34' and the closest point to the furcation 36'. The measurement designated by the letter "B" represents the distance between the pulp chamber ceiling 32' to the closest point to the furcation 36'. The measurement designated by the letter "C" represents the distance from the buccal cusp tip 24' of the molar 20' to the closest point to the furcation 36'. The measurement designated by the letter "D" represents the distance from the buccal cusp tip 24' to the pulp chamber floor 34'. The measurement designated by the letter "E" represents the distance from the buccal cusp tip 24' to the pulp chamber ceiling 32'. The measurement designated by the letter "F" represents the distance between the pulp chamber ceiling 32' and the pulp chamber floor 34'. The x-ray analysis of the maxillary molars 20' also noted whether the pulp chamber ceiling 32' was located above, below or at the level of the Cemento-Enamel Junction (CEJ).

The results of the study are set forth in Tables I and II below. Table I shows the mean standard deviation and percentage variants for each measurement for maxillary molars. Table II shows the mean, standard deviation and percentage variants for mandibular molars.

TABLE I

Mean Measurements in mm for Maxillary Molars.

| N = 100 | A | B | C | D = (C − A) | E = (C − B) | F = (B − A) |
|---|---|---|---|---|---|---|
| Mean | 3.05 | 4.91 | 11.15 | 8.08 | 6.24 | 1.88 |
| SD | 0.79 | 1.06 | 1.21 | 0.88 | 0.88 | 0.69 |
| % Variance | 25.8 | 21.6 | 10.9 | 10.9 | 14.11 | 36.5 |

TABLE II

Mean Measurements in mm for Mandibular Molars.

| N = 100 | A | B | C | D = (C − A) | E = (C − B) | F = (B − A) |
|---|---|---|---|---|---|---|
| Mean | 2.96 | 4.57 | 10.9 | 7.95 | 6.36 | 1.57 |
| SD | 0.78 | 0.91 | 1.21 | 0.79 | 0.93 | 0.68 |
| % Variance | 26 | 20 | 11.1 | 9.94 | 14.6 | 43 |

As shown above in Tables I and II, despite the various sizes of molars, there appears to be a relatively uniform distance between the cusp tip of a molar and the pulp chamber ceiling. This cusp tip to pulp chamber ceiling height averages approximately 6 mm in distance. The distance between the pulp chamber floor and the furcation averages approximately 3 mm and the height of the pulp chambers average approximately 1.5 to 2.0 mm. Moreover, the pulp chamber ceiling and the Cemento-Enamel Junction were at the same level of the tooth in 98% of maxillary molars and 97% of mandibular molars.

A review of endodontic literature contains only a few studies related to measuring anatomical landmarks for pulp chambers of teeth. Due to large variants in the overall size of molars, those skilled in the art may have assumed that the morphology and arch position of the two and the dimensions of the pulp chamber would also show great variability, so that the measurements would be clinically useless. The present study, however, disclosed that the dimensions for both maxillary and mandibular molar teeth are very similar.

The results of the present study are supported by Sterrett J. B., Pelletier H., and Russell C. M., "Tooth Thickness at the Furcation Entrance of Lower Molars," Journal of Clinical Peridontal 1996; 23: 621–7. Sterrett reported that the average distance from the pulp chamber to the furcation was 2.83 mm for mandibular first molars and 2.88 millimeter for mandibular second molars. Majzoub and Kon measured maxillary molars and found that the distance from the pulp chamber floor to the furcation was less than or equal to 3 mm in 86% of the teeth measured. Majzoub Z., Kon, S., "Tooth Morphology Following Root Resection Procedures in Maxillary First Molars," Journal of Clinical Peridontal 1992; 63: 290–6. These earlier articles support the conclusions of the present study which found that the distance between the pulp chamber floor to the furcation averages 3.05 mm for maxillary molars and 2.96 mm for mandibular molars.

Figure 3A:
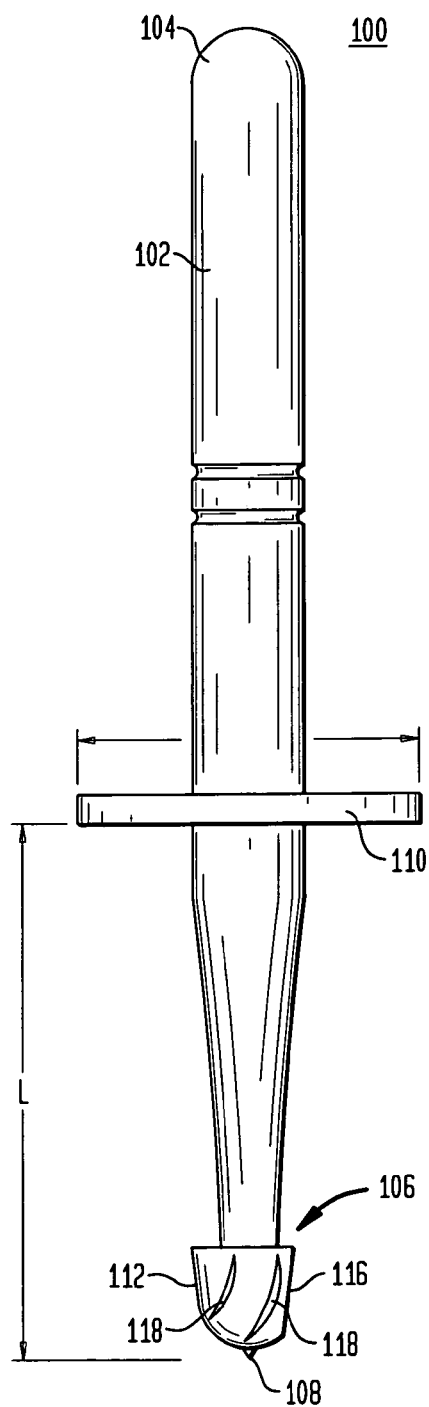
FIGS. 3A and 3B show front elevational views of an endodontic instrument having a cutting head for accessing a pulp chamber, in accordance with certain preferred embodiments of the present invention.
Figure 3B:
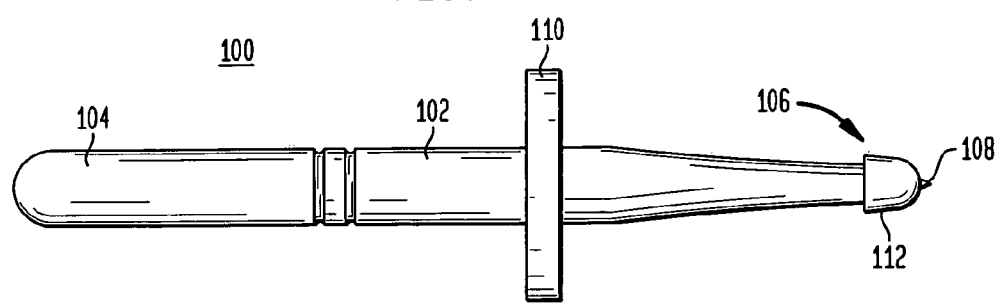

Based upon the results of the study, an endodontic instrument has been invented that safely and reliably drills into the pulp chambers of mandibular and maxillary molars without perforating the pulp chamber floor or the furcation of the tooth. FIGS. 3A and 3B show a preferred endodontic instrument 100 that is used to drill an access opening into the pulp chamber of mandibular and maxillary molars. The instrument 100 has an elongated shaft 102 with an upper end 104, a lower end 106 and a pointed tip 108 provided at the lower end 106 of the shaft 102. The endodontic instrument 100 also includes a stop 110 fixed thereto. In certain preferred embodiments, the stop 110 is made of a rigid material and is permanently fixed to an exterior surface of shaft 102. In other words, the stop is designed to permanently remain at a fixed distance from the pointed tip of the instrument.

Figure 4:
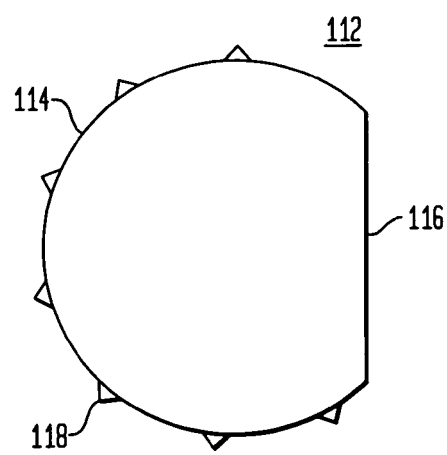
FIG. 4 shows a cross-sectional view of the cutting head of the endodontic instrument of FIGS. 3A and 3B.

The endodontic instrument 100 also preferably includes a cutting head 112 located along the shaft 102 adjacent the pointed tip 108. The cutting head 112 is preferably permanently affixed to the shaft and has a cross-sectional diameter that extends beyond the cross-sectional diameter of the shaft 102 in the vicinity of the lower end of the shaft. The cutting head may be integrally connected with the shaft 102 and may be made of the same material as the shaft. Referring to FIG. 4, in certain preferred embodiments the cutting head 112 has an annular cutting surface extending about a first circumferential portion 114 of the cutting head and a flat, non-cutting surface extending about a second circumferential portion 116 of the cutting head. The cutting head also includes cutting edges 118 provided on the annular cutting surface thereof. The cutting edges 118 may be in the form of helical threads. In certain preferred embodiments, the annular cutting surface includes a spherical cutting surface having cutting edges provided thereon.

Referring to FIG. 3A, the endodontic instrument 100 is preferably adapted for drilling access openings into the pulp chambers of maxillary and mandibular molars. Based upon the above-mentioned study measuring critical morphology of molar pulp chambers, it has been determined that the average distance between the cusp tips and the pulp chamber ceiling of molars is approximately 6 mm. Moreover, it has been determined that the average height of a pulp chamber of a molar is approximately 2 mm. As a result, the endodontic instrument 100 (FIG. 3A) of the present application has been designed so that the fixed stop 110 is preferably at a distance "L" of approximately 6–8 mm from the pointed tip 108. In certain preferred embodiments, the flat non-cutting surface 116 tapers inwardly from the upper end toward the pointed lower end of the instrument 100. In more preferred embodiments, the flat non-cutting surface 116 tapers inwardly at approximately 4–6°. In even more preferred embodiments, the flat surface 116 tapers inwardly at about 5°.

Figure 5:
FIG. 5 shows a front elevational view of a shaper bur for shaping an inner wall of an opening formed in a tooth, in accordance with certain preferred embodiments of the present invention.

FIG. 5 shows a shaper bur 130 including a shaft 132 having an upper end 134 and a lower end 136. The lower end of the shaper bur 130 has an exterior surface that is roughened. In highly preferred embodiments, the exterior surface includes a diamond material. As will be described in more detail below, after accessing the pulp chamber using the endodontic instrument shown in FIGS. 3A and 3B, the shaper bur is used to smooth out the interior axial wall of the access opening.

Figure 6A:
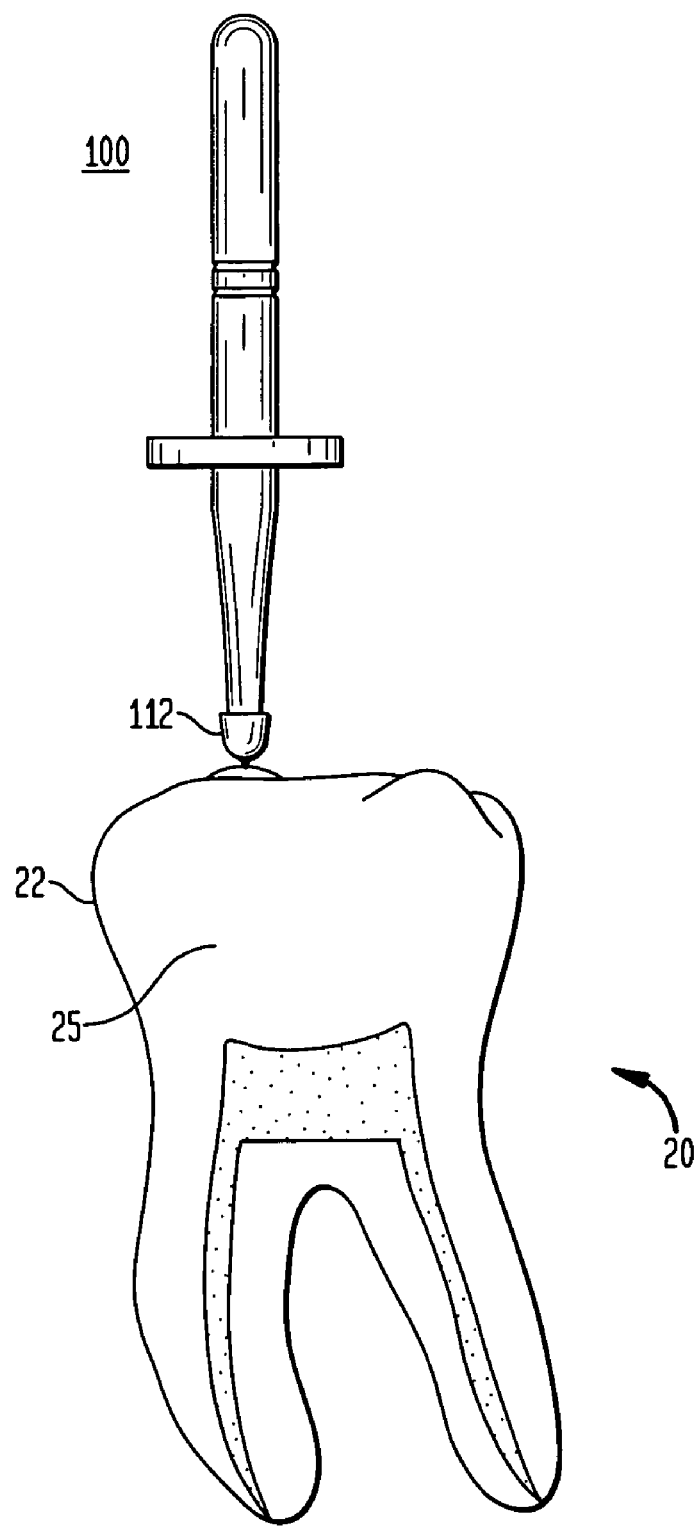
FIGS. 6A and 6B show a method of accessing a pulp chamber, in accordance with certain preferred embodiments of the present invention.
Figure 6B:
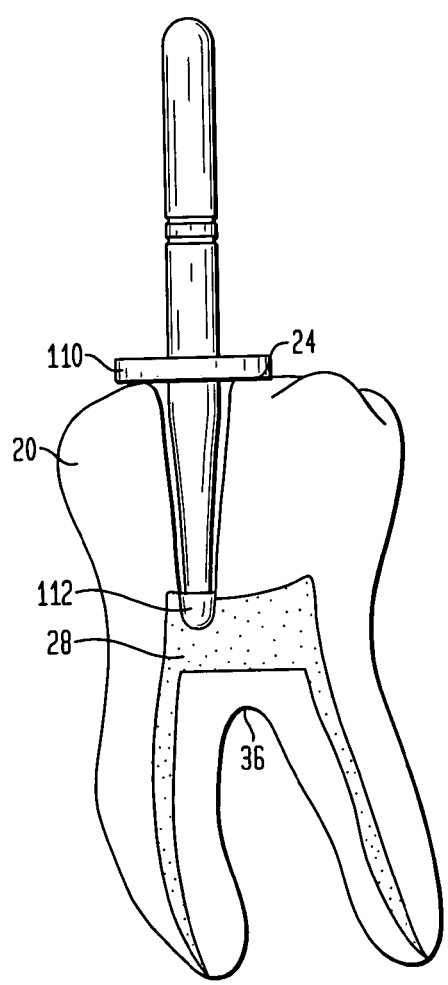

Referring to FIG. 6A, in certain preferred embodiments, a pulp chamber 28 of a molar 20 is accessed by using the endodontic instrument 100 shown and described above in FIGS. 3A and 3B. In preferred embodiments, this is accomplished by abutting the pointed tip 108 of endodontic instrument 100 against the molar 20. The pointed tip 108 provides an anchor point about which the endodontic instrument 100 may rotate. The upper end of the endodontic instrument is preferably connected to a drill for rapidly rotating the endodontic instrument. As the endodontic instrument 100 is rotated, a downward force is applied through the instrument and onto the crown of the tooth so that the cutting head 112 cuts through the dentin portion 25 of molar 20. Referring to FIG. 6B, the cutting head 112 continues to cut into the pulp chamber 28 until the bottom of stop 110 abuts against one or more cusp tips 24 at the top of crown 20. The stop 110 abutting against the one or more cusp tips 24 prevents further advance of the cutting head 112. In preferred embodiments, the stop is affixed approximately 6–8 mm from the pointed tip of the cutting instrument and is more preferably affixed approximately 7 mm from the tip of the endodontic instrument. Using the above-mentioned dimensions will enable a dentist to safely cut into the pulp chamber of molars without perforating the furcation 36.

Figure 7:
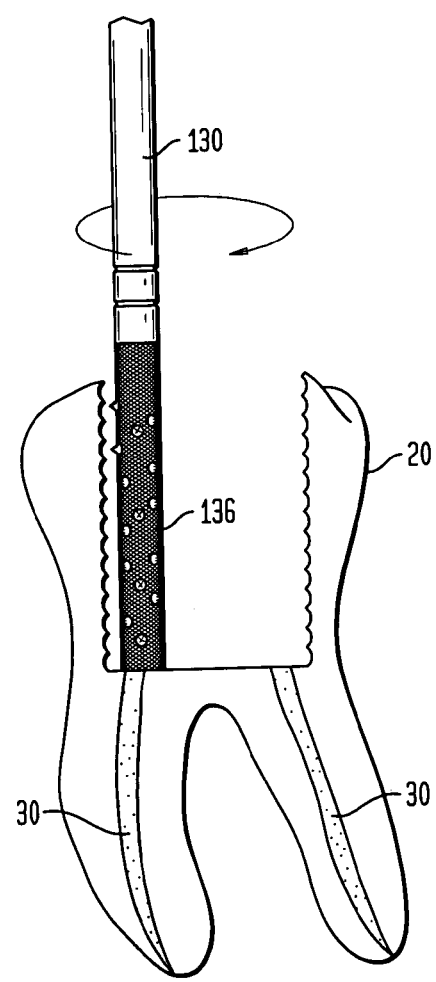
FIG. 7 shows a method of cleaning a pulp chamber, in accordance with certain preferred embodiments of the present invention.

Referring to FIG. 7, after access to the pulp chamber has been obtained, the shaping bur 130 is used to hollow out the access opening. The shaping bur preferably includes a roughened portion 136 that smoothes out the interior axial walls of the access opening for exposing and providing visual access to the upper ends of the root canals 30 of the molar. Once the root canals have been exposed, endodontic files may be used for cleaning out the root canals.

Figure 8A:
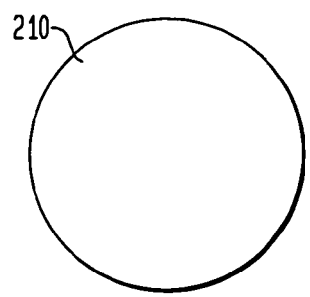
FIG. 8A shows a stop for an endodontic instrument having a circular shape, in accordance with certain preferred embodiments of the present invention.
Figure 8B:
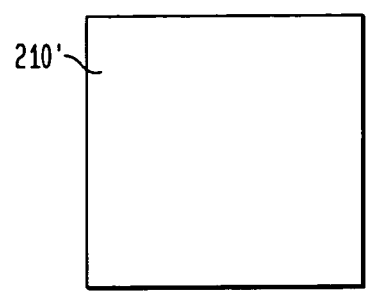
FIG. 8B shows a stop for an endodontic instrument having a square shape, in accordance with certain preferred embodiments of the present invention.
Figure 8C:
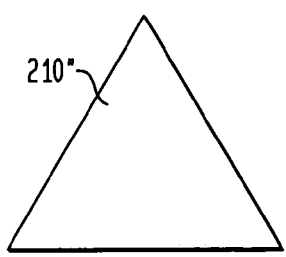
FIG. 8C shows a stop for an endodontic instrument having a triangular shape, in accordance with certain preferred embodiments of the present invention.

As noted above, the stop for the endodontic instrument of the present invention may have different geometric shapes. FIG. 8A shows a stop 210 having the cross-sectional shape of a circle. FIG. 8B shows a stop 210' having the cross-sectional shape of a polygon which is a square. FIG. 8C shows a stop 210" having a triangular shape. In other preferred embodiments, any geometric shape may be used for the stop. Preferably, the top and bottom faces of the stop are substantially parallel to one another.

Figure 9A:
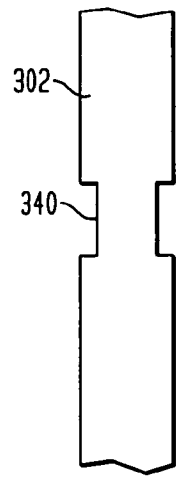
FIGS. 9A and 9B show a shaft for an endodontic instrument having a notch formed therein for engaging a stop, in accordance with certain preferred embodiments of the present invention.
Figure 9B:
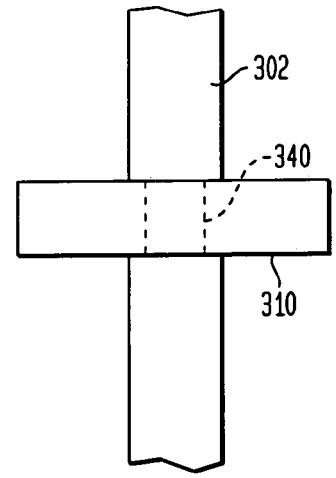

Referring to FIG. 9A, in other preferred embodiments of the present invention, an endodontic instrument includes a shaft 302 having a notch or groove 340 formed therein. Referring to FIG. 9B, a stop 310 is fixed to shaft 302 with the stop 310 engaging the groove 340 of the shaft.

Although the invention herein has been described with reference to particular embodiments, it is to be understood that these embodiments are merely illustrative of the principles and applications of the present invention. For example, the endodontic instrument of the present application can be preferably used to drill into the pulp chamber of any tooth having a furcation such as a bicuspid or a molar. It is therefore to be understood that numerous modifications may be made to the illustrative embodiments and that other arrangements may be devised without departing from the spirit and scope of the present invention as defined by the appended claims.

The invention claimed is:

1. An endodontic instrument comprising:
   an elongated shaft having an upper end and a lower end;
   a stop permanently fixed to said shaft at a distance between 6–8 mm from said lower end;
   a cutting head located along said shaft adjacent said lower end, wherein said cutting head has an annular cutting surface extending about a first circumferential portion of said cutting head and a flat non-cutting surface extending about a second circumferential portion of said cutting head.

2. The endodontic instrument as claimed in claim 1, wherein said stop is permanently fixed to said shaft at a distance between 6.5–7.5 mm from said lower end.

3. The endodontic instrument as claimed in claim 2, wherein said stop is permanently fixed to said shaft at a distance between 6.75–7.25 mm from said lower end.

4. The endodontic instrument as claimed in claim 3, wherein said stop is permanently fixed to said shaft at a distance of approximately 7 mm from said lower end.

5. The endodontic instrument as claimed in claim 1, further comprising a pointed tip provided at the lower end of said shaft.

6. The endodontic instrument as claimed in claim 1, wherein said stop is rigid.

7. The endodontic instrument as claimed in claim 1, wherein said shaft has an exterior surface including an annular groove and said stop is at least partially secured in the annular groove.

8. The endodontic instrument as claimed in claim 1, wherein the flat non-cutting surface of said cutting head tapers inwardly between the upper and lower ends of said shaft.

9. The endodontic instrument as claimed in claim 8, wherein the flat non-cutting surface tapers inwardly at approximately 4–6 degrees.

10. The endodontic instrument as claimed in claim 1, wherein the annular cutting surface of said cutting head has cutting edges formed therein.

11. The endodontic instrument as claimed in claim 1, wherein said cutting head has a cross-section diameter that is greater than a cross-sectional diameter of said shaft.

12. The endodontic instrument as claimed in claim 1, wherein said stop is circular.

13. The endodontic instrument as claimed in claim 1, wherein said stop has a polygon shape.

14. An endodontic instrument adapted for accessing a pulp chamber of a molar comprising:
    an elongated shaft having an upper end and a lower end;
    a pointed tip provided at the lower end of said shaft;
    a rigid stop permanently fixed to said shaft at a distance between 6–8 mm from said pointed tip;
    a cutting head located along said shaft adjacent said pointed tip, wherein said cutting head has a spherical cutting surface extending about a first circumferential portion of said cutting head and a flat non-cutting surface extending about a second circumferential portion of said cutting head.

15. The endodontic instrument as claimed in claim 14, wherein the spherical cutting surface of said cutting head has cutting edges formed therein.

16. The endodontic instrument as claimed in claim 14, wherein said stop is fixed to said shaft at a distance between 6.5–7.5 mm from said pointed tip.

17. The endodontic instrument as claimed in claim 16, wherein said stop is fixed to said shaft at a distance between 6.75–7.25 mm from said pointed tip.

18. The endodontic instrument as claimed in claim 17, wherein said stop is fixed to said shaft at a distance of approximately 7 mm from said pointed tip.

19. The endodontic instrument as claimed in claim 14, wherein when accessing the pulp chamber of said molar, said stop is adapted for abutting against a cusp tip of said molar for limiting forward movement of said cutting head so as to prevent said cutting head from passing through a floor of said pulp chamber.

20. The endodontic instrument as claimed in claim 14, wherein said shaft has an exterior surface including an annular groove and said stop is at least partially secured in the annular groove.

21. An endodontic instrument comprising:
    an elongated shaft having an upper end and a lower end;
    a pointed tip provided at the lower end of said shaft;
    a rigid stop permanently fixed to said shaft and spaced from said pointed tip;
    a cutting head provided at the lower end of said shaft adjacent said pointed tip, wherein said cutting head has a spherical cutting surface extending about a first circumferential portion of said cutting head and a flat non-cutting surface extending about a second circumferential portion of said cutting head.

22. The endodontic instrument as claimed in claim 21, wherein said pointed tip protrudes from the spherical cutting surface of said cutting head.

* * * * *